United States Patent [19]
Edwards

[11] Patent Number: 5,836,906
[45] Date of Patent: Nov. 17, 1998

[54] METHOD AND APPARATUS FOR TREATMENT OF AIR WAY OBSTRUCTIONS

[75] Inventor: Stuart D. Edwards, Los Altos, Calif.

[73] Assignee: SOMNUS Medical Technologies, Inc., Sunnyvale, Calif.

[21] Appl. No.: 651,800

[22] Filed: May 22, 1996

Related U.S. Application Data

[63] Continuation-in-part of Ser. No. 642,053, May 3, 1996, which is a continuation-in-part of Ser. No. 606,195, Feb. 23, 1996, Pat. No. 5,683,360.

[51] Int. Cl.$^6$ .................................................. A61M 1/00
[52] U.S. Cl. ................................................................ 604/22
[58] Field of Search .............................. 604/22, 19–20, 604/164, 280, 53; 606/39, 32, 45; 607/96, 98, 134; 601/2

[56] References Cited

U.S. PATENT DOCUMENTS

| | | | |
|---|---|---|---|
| 3,901,241 | 8/1975 | Allen | 128/303.1 |
| 4,011,872 | 3/1977 | Komiya | 128/303.14 |
| 4,411,266 | 10/1983 | Cosman | 128/303.18 |
| 4,423,812 | 1/1984 | Sato | 206/387 |
| 4,532,924 | 8/1985 | Auth et al. | 128/303.17 |
| 4,565,200 | 1/1986 | Cosman | 128/642 |
| 4,901,737 | 2/1990 | Toone | 128/848 |

(List continued on next page.)

FOREIGN PATENT DOCUMENTS

| | | |
|---|---|---|
| 139 607 | 5/1985 | European Pat. Off. . |
| 608 609 | 8/1994 | European Pat. Off. . |
| WO 92/10142 | 6/1992 | WIPO . |
| WO 93/08755 | 5/1993 | WIPO . |
| WO 94/10925 | 5/1994 | WIPO . |
| WO 94/26178 | 11/1994 | WIPO . |
| WO 95/18575 | 7/1995 | WIPO . |
| WO 95/19142 | 7/1995 | WIPO . |
| WO 96/29946 | 10/1996 | WIPO . |

OTHER PUBLICATIONS

Kaneko, et al., *Physiological Laryngeal Pacemaker*, May 1985, Trans Am Soc Artif Intern Organs, vol. XXXI, pp. 293–296.

Mugica, et al., *Direct Diaphragm Stimulation*, Jan., 1987, PACE, vol. 10, pp. 252–256.

Mugica, et al., Neurostimulation: An Overview, Chapter 21, *Preliminary Test of a Muscular Diaphragm Pacing System on Human Patients*, 1985, pp. 263–279.

Prior, et al., *Treatment of Menorrhagia by Radiofrequency Heating*, 1991, Int. J. Hyperthermia, vol. 7, pp. 213–220.

Nochomovitz, et al., *Electrical Activation of the Diaphragm*, Jun. 1988, Clinics in Chest Medicine, vol. 9, No. 2, pp. 349–358.

Rice, et al., Endoscopic Paranasal Sinus Surgery, Chapters 5, *Functional Endoscopic Paranasal Sinus Surgery, The Technique of Messerklinger*, Raven Press, 1988, pp. 75–104.

Rice et al., Endoscopic Paranasal Sinus Surgery, Chapters 6, *Total Endoscopic Sphenoethmoidectomy, The Technique of Wigand*, Raven Press, 1988, pp. 105–125.

*Primary Examiner*—Michael Buiz
*Assistant Examiner*—Manuel Mendez
*Attorney, Agent, or Firm*—Wilson Sonsini Goodrich and Rosati

[57] ABSTRACT

An apparatus ablates at least a portion of an interior of a body structure with a reduced chance of body structure infection. A catheter is provided with a catheter tissue interface surface and a port formed in the catheter tissue interface surface. An electrode is at least partially positioned in the interior of the catheter and is configured to be advanced and retracted in and out of the port. The electrode includes an electrode electromagmetic energy delivery surface. A disinfectant medium introduction member coupled to a source of a disinfectant medium and includes a distal end that is configured to extend into an oral cavity. An electrode advancement and retraction device is at least partially positioned in the interior of the catheter. A cable is coupled to the electrode.

40 Claims, 18 Drawing Sheets

U.S. PATENT DOCUMENTS

| | | | |
|---|---|---|---|
| 4,906,203 | 3/1990 | Margrave et al. | 439/188 |
| 4,907,589 | 3/1990 | Cosman | 606/34 |
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,328,467 | 7/1994 | Edwards et al. | 604/95 |
| 5,334,196 | 8/1994 | Scott et al. | 606/138 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,366,490 | 11/1994 | Edwards et al. | 607/99 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,433,739 | 7/1995 | Sluijter et al. | 607/99 |
| 5,435,805 | 7/1995 | Edwards et al. | 604/22 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et al. | 604/22 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |

Average Shrinkage in Z Direction = 20%

METHOD AND APPARATUS FOR TREATMENT OF AIR WAY OBSTRUCTIONS

CROSS REFERENCE TO RELATED APPLICATIONS

This application is a continuation-in-part application of U.S. application Ser. No. 08/642,053, which still pending, entitled "METHOD FOR TREATMENT OF AIRWAY OBSTRUCTIONS", filed May 3, 1996, which is a continuation-in-part application of U.S. patent application Ser. No. 08/606,195, filed Feb. 23, 1996, entitled "Method for Treatment of Airway Obstructions", and now U.S. Pat. No. 5,683,360.

BACKGROUND OF THE INVENTION

1. Field of the Invention

This invention relates to an apparatus and method for ablating an interior section of a body member, and more particularly to an apparatus and method for ablating an interior section of a tongue or soft tissue structure while reducing the infection of the ablated tongue or soft tissue.

2. Description of Related Art

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. In one procedure the jaw is dislodged and pulled forward, in order to gain access to the base of the tongue. These procedures may be effective but the risk of surgery in these patients can be prohibitive and the procedures are often unacceptable to the patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in Direct *Diaphragm Stimulation* by J. Mugica et al. PACE vol. 10 January–February 1987, Part II, *Preliminary Test of a Muscular Diaphragm Pacing System on Human Patients* by J. Mugica et al. from Neurostimulation: An Overview 1985 pp. 263–279 and *Electrical Activation of Respiration by Nochomovitez* IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue inferiorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

There is a need for a method and apparatus to treat airway obstruction disorders. There is a further need for a method and apparatus which delivers sufficient electromagnetic energy to an interior of a body structure, including but not limited to the tongue and soft palate tissue, to treat airway obstruction disorders while introducing a disinfectant medium into an oral cavity. Still a further need exists to reduce the volume of the tongue or soft palate tissue while reducing the chance of infection.

SUMMARY OF THE INVENTION

Accordingly, an object of the invention is to provide a method and apparatus to treat airway obstructions.

Another object of the invention is to provide a method and apparatus for ablating an interior of a body structure found in the oral cavity.

Still another object of the invention is to provide a method and apparatus for ablating an interior of a tongue in a environment that has been selectively disinfected to reduce or eliminate infection.

A further object of the invention is to provide a method and apparatus for ablating an interior section of a tongue that provides for at least a portion of the oral cavity to be disinfected to a selected level of disinfection.

Another object of the invention is to provide a method and apparatus for ablating an interior section of a tongue while reducing chances of infection.

These and other objects of the invention are achieved in an ablation apparatus which ablates at least a portion of an interior of a body structure that is configured to reduce a chance of body structure infection. A catheter is provided with a catheter tissue interface surface and a port formed in the catheter tissue interface surface. An electrode is at least partially positioned in the interior of the catheter and is configured to be advanced and retracted in and out of the port. The electrode includes an electrode electromagnetic energy delivery surface. A disinfectant member coupled to a source of a disinfectant medium and includes a distal end that is configured to extend into an oral cavity. An electrode advancement and retraction device is at least partially positioned in the interior of the catheter. A cable is coupled to the electrode.

In one embodiment of the invention, a method is provided for reducing a volume of a body structure while reducing the chances of body structure infection. An ablation apparatus is provided that includes a catheter with a catheter tissue interface surface, and an electrode at least partially positioned in an interior of the catheter and advanceable and retractable to and from the catheter into an interior of the body member. A disinfectant member that is configured to introduce a disinfectant medium into at least a portion of an oral cavity is also provided. The disinfectant member and the ablation apparatus are introduced into the oral cavity. At least a portion of the oral cavity is disinfected sufficiently to reduce an infection of the body member. The electrode is introduced from the interior of the catheter through a body structure external surface into the interior of the body structure. Sufficient energy is delivered from the electrode into the interior of the body structure to ablate a portion of the interior of the body structure. The electrode is retracted from the interior of the body structure.

The disinfectant member can be integrated with the catheter or be a separate device. Thus, the two can be introduced into the oral cavity simultaneously or introduced at different times. The disinfectant member can be an introducer with a lumen that is coupled to a disinfectant agent including but not limited to Peridex. Additionally, the disinfectant member can be an optical fiber that delivers UV energy to the oral cavity. All or only a portion of the oral cavity can be disinfected to a desired level in order to reduce infection of the ablated body structure. The body structure can be the tongue or soft palate tissue, including but not limited to the uvula, tonsils and the like.

DETAILED DESCRIPTION

Figure 1:
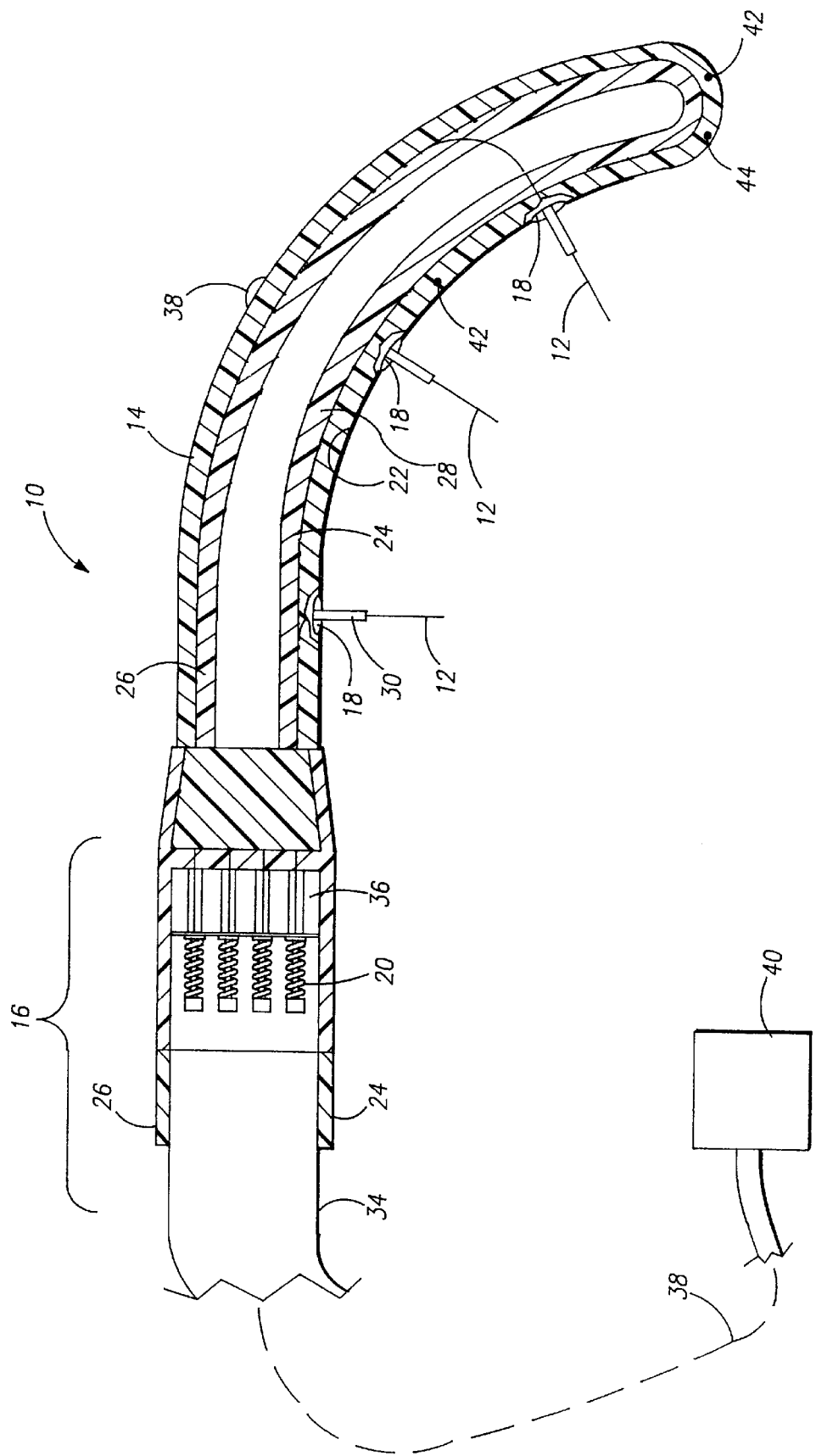
FIG. 1 is a perspective of the ablation apparatus of the present invention illustrating a catheter tissue interface surface.
Figure 2:
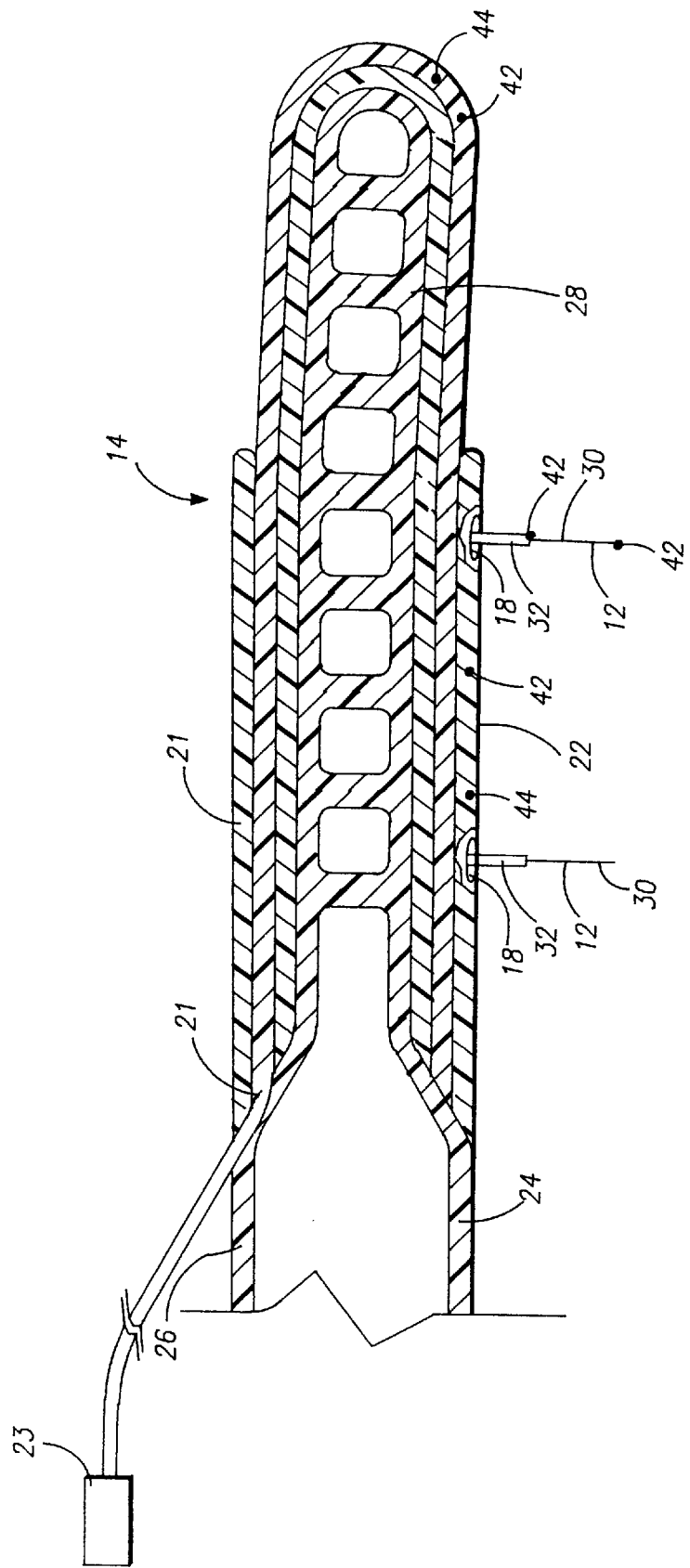
FIG. 2 is cross-sectional view illustrating the catheter and connector of the ablation apparatus shown in FIG. 1(a).

Referring to FIGS. 1 and 2, an ablation apparatus 10 for debulking the tongue, lingual tonsils, and/or soft palate tissue, including but not limited to the uvula, is illustrated. Ablation apparatus 10 can be positioned so that one or more electrodes 12, which may be needle electrodes, are introduced into an interior of the tongue through a surface of the tongue. Ablation apparatus 10 may include atraumatic intubation with or without visualization, provide for the delivery of oxygen or anesthetics, and can be capable of suctioning blood or other secretions. It will be appreciated that ablation apparatus 10 is used to treat a variety of different obstructions in the body where passage of gas is restricted. One embodiment is the treatment of sleep apnea using electrodes 12 to ablate selected portions of the tongue, lingual tonsils and/or adenoids by the use of RF, microwave, and the like. In this regard, ablation apparatus 10 can be used to ablate targeted masses including but not limited to the tongue, tonsils, turbinates, soft palate tissues, hard tissue and mucosal tissue. In one embodiment, ablation apparatus 10 is used to ablate an interior region of the tongue, causing it to become debulked in order to increase the cross-sectional area of the airway passage. A disinfectant medium introduction member introduces a disinfectant medium in the oral cavity in order to reduce infection of the ablated body member.

Prior to debulking the tongue, a presurgical evaluation may be performed including a physical examination, fiber optic pharyngoscopy, cephalometric analysis and polygraphic monitoring. The physical examination emphasizes the evaluation of the head and neck. It also includes a close examination of the nasal cavity to identify obstructing deformities of the septum and turbinate; oropharyngeal obstruction from a long, redundant soft palate or hypertrophic tonsils; and hypopharyngeal obstruction from a prominent base of the tongue.

Ablation apparatus 10 includes a catheter 14, a handle 16, one or more electrodes 12 extending from different ports 18 formed along a longitudinal surface of catheter 14, or from a distal end of electrode 12. An electrode advancement and retraction device 20 is provided. Cabling is coupled to electrodes 12.

Controlled volumetric reduction of the tongue, under feedback control is used to achieve an effective opening in the airway passage. A variety of different pain killing medicaments, including but not limited to Xylocaine. A digital ultrasonic measurement system can be used. The ultrasound measurement quantifies biological shape changes, provides ultrasonic transmission and reception, uses piezoelectric transducers (crystals) and provides time of flight data.

A disinfectant medium introduction member 21 is also introduced into the oral cavity. Disinfectant medium introduction member 21 can be introduced before, after or during the introduction of ablation apparatus 10 into the oral cavity. Additionally, disinfectant medium introduction member 21 can be removed at the same time or at a different time that ablation apparatus 10 is removed from the oral cavity. Disinfectant medium introduction member 21 can be included in ablation apparatus 10, in an interior of catheter 14 or at an exterior of catheter 14, and may be an introducer with a lumen configured to introduce a disinfectant agent from a disinfectant agent source 23 into all or a selected portion of the oral cavity. Disinfectant medium introduction member 21 can be capable of movement within the oral cavity in order to provide for disinfection of all or only a portion of the oral cavity. For purposes of this disclosure, the oral cavity is that body internal environment where infectious germs may be introduced into the ablated tongue, soft tissue structure, and the like. Disinfectant medium introduction member 21 may be slideably positioned in catheter 14 or at its exterior. Alternatively, disinfectant medium introduction member 21 can be an optical fiber coupled to a light energy source, including but not limited to a UV source 25. The optical fiber can also be slideably positioned in the oral cavity. The optical fiber is configured to provide for the selective disinfection of all or only a portion of the oral cavity and can have a variety of different distal ends to achieve this purpose.

Suitable disinfectant agents include but are not limited to Peridex, an oral rinse containing 0.12% chlorhexidine glucinate (1, 1'-hexanethylenebis[5-(p-chlorophenyl) biganide} di-D-gluconate in a base containing water, 11.6% alcohol, glycerin, PEG 40 sorbitan arisoterate, flavor, dosium saccharin, and FD&C Blue No. 1.

It will be appreciated that a variety of different disinfectants can be employed, including other electromagnetic wavelengths, and various chemical compositions.

Electrodes 12 are at least partially positioned in an interior of catheter 14. Each electrode 12 is advanced and retracted through a port 18 formed in an exterior surface of catheter 14. Electrode advancement and retraction device advances electrodes 12 out of catheter 14, into an interior of a body structure and retracted back into catheter 14. Although the body structure can be any number of different structures, the body structure will hereafter be referred to as the tongue. Electrodes 12 pierce an exterior surface of the tongue and are directed to an interior region of the tongue. Sufficient electromagnetic energy is delivered by electrodes 12 to the interior of the tongue to cause the tongue to become sufficiently ablated and debulked. Electrodes 12 can be hollow to receive a variety of different infusion mediums, including but not limited to saline. Electrodes 12 may be limited in the distance that they can be advanced into the tongue. This is achieved with an insulation sleeve, a structure located on electrodes 12 which limits their advancement, or a structure coupled to catheter which limits the advancement of electrodes 12, such as a stop and the like.

The disinfectant medium can be introduced prior to ablation, during ablation and/or after the ablation. It can be delivered continuously. The level of disinfection of the oral cavity is selectable as is the volume of the oral cavity that is disinfected. The degree of disinfection varies. Disinfection is provided to reduce infection of the ablated body structure.

Electrodes 12 can include a central lumen for receiving a variety of fluids that can be introduced into the interior of the tongue, as well as a plurality of fluid delivery ports. In one embodiment, the disinfectant agent is introduced through electrodes 12 into the interior of the selected body structure. One suitable fluid is an electrolytic solution. Instead of direct contact with tissue and electrode 12 for the delivery of thermal energy, a cooled electrolytic solution can be used to deliver the thermal energy to the tissue. The electrolytic solution may be cooled in the range of about 30 to 55 degrees C.

Catheter 14 includes a catheter tissue interface surface 22, a cooling medium inlet conduit 24 and a cooling medium exit conduit 26 extending through an interior of catheter 14. Ports 18 are formed in the exterior of catheter 14, and are preferably formed on catheter tissue interface surface 22. Ports 18 are isolated from a cooling medium flowing in inlet and outlet conduits 24 and 26. Cooling medium inlet and exit conduits 24 and 26 are configured to provide a cooled section of catheter tissue interface surface 22 of at least 1 to 2 cm$^2$. More preferably, the cooled section of catheter tissue interface surface 22 is at least equal to the cross-sectional diameter of the underlying zone of ablation.

The size of the cooled section of catheter tissue interface surface 22 varies for each patient. The size is sufficient enough to minimize swelling of the tongue following the delivery of electromagnetic energy. The reduction of swelling can be 50% or greater, 75% or greater, and 90% and greater. The amount of cooling provided is sufficient to enable the patient to return home shortly after the debulking procedure is performed, and not run the risk of choking on the tongue. It has been found that by providing a sufficient level of cooling over a relatively large area, the amount of ablation in an interior region of the tongue is enhanced. By providing a sufficiently large enough cooled section of catheter tissue interface surface 22, an adenomas response is minimized.

Figure 3:
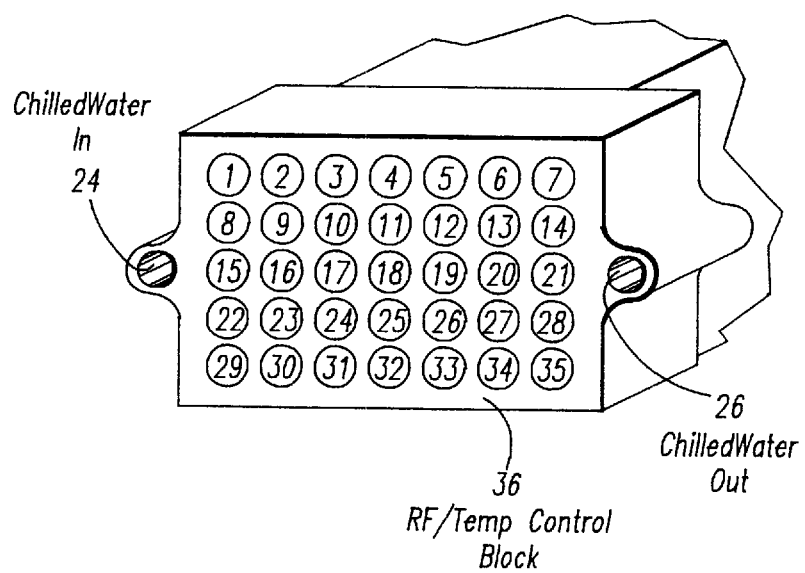
FIG. 3 is a perspective view of the connector illustrated in FIG. 1(a).
Figures 4, 5:
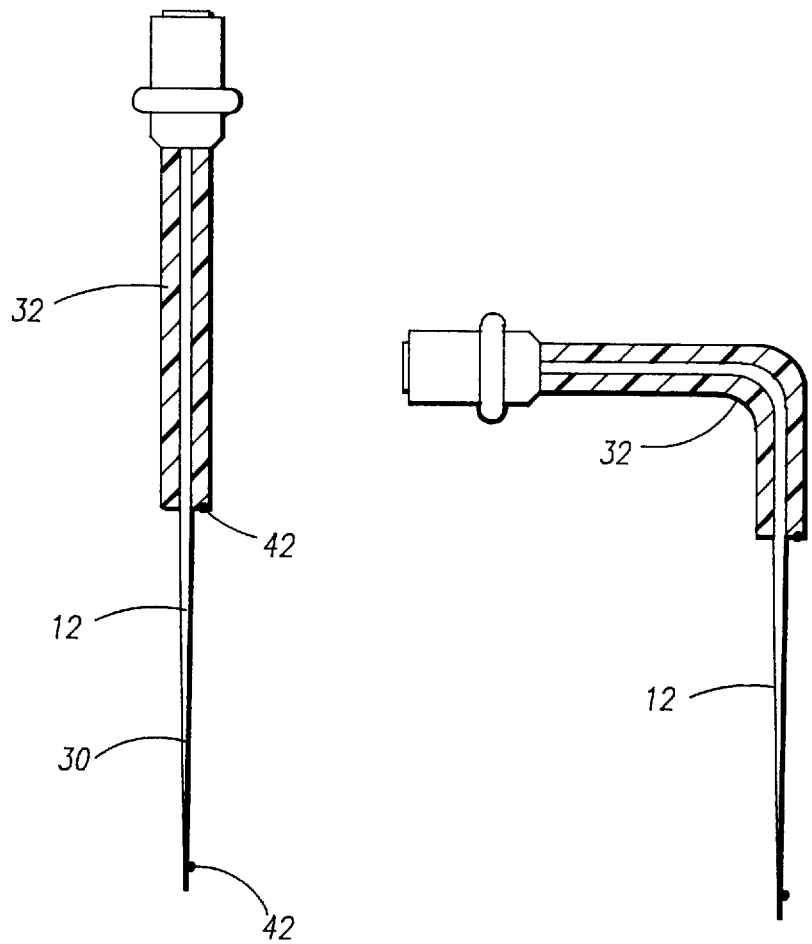
FIG. 4 is a perspective view of a needle electrode associated with the ablation apparatus illustrated in FIG. 1(a).
FIG. 5 is a perspective view of a flexible needle electrode utilized with the methods of the present invention.

An electromagnetic energy delivery surface 30 of electrode 12 can be adjusted by inclusion of an adjustable or non-adjustable insulation sleeve 32 (FIGS. 3, 4, and 5). Insulation sleeve 32 can be advanced and retracted along the exterior surface of electrode 12 in order to increase or decrease the length of the electromagnetic energy delivery surface 30. Insulation sleeve 32 can be made of a variety of materials including but not limited to nylon, polyimides, other thermoplastics and the like. The size of electromagnetic energy delivery surface 30 can be varied by other methods including but not limited to creating a segmented electrode with a plurality of electrodes that are capable of being multiplexed and individually activated, and the like.

Handle 16 is preferably made of an insulating material. Electrodes 12 are made of a conductive material such as stainless steel. Additionally, electrodes 12 can be made of a shaped memory metal, such as nickel titanium, commercially available from Raychem Corporation, Menlo Park, Calif. In one embodiment, only a distal end of electrode 12 is made of the shaped memory metal in order to effect a desired deflection. When introduced into the oral cavity, catheter 14 can be advanced until a patient's gag response is initiated. Catheter 14 is then retracted back to prevent patient's gagging. The distal end of electrode 12 can be semi-curved. The distal end can have a geometry to conform to an exterior of the tongue.

Catheter 14 can be malleable in order to conform to the surface of the tongue when a selected ablation target site is selected. An encapsulated soft metal, such as copper, or an annealed metal/plastic material can be used to form malleable catheter 14. All or a portion of catheter 14 may be malleable or made of a shaped memory metal.

For many applications it is desirable for a distal end 14' of catheter 14 to be deflectable. This can be achieved mechanically or with the use of memory metals. A steering wire, or other mechanical structure, can be attached to either the exterior or interior of distal end 14'. In one embodiment, a deflection knob located on handle 16 is activated by the physician causing a steering wire to tighten. This imparts a retraction of distal end 14', resulting in its deflection. It will be appreciated that other mechanical devices can be used in place of the steering wire. The deflection may be desirable for tissue sites with difficult access.

Handle 6 can comprise a connector 34 coupled to retraction and advancement device 20. Connector 34 provides a coupling of electrodes 12 to power, feedback control, temperature and/or imaging systems. An RF/temperature control block 36 can be included.

In one embodiment, the physician moves retraction and advancement device 20 in a direction toward a distal end of connector 34. Electrodes 12 can be spring loaded. When retraction and advancement device 20 is moved back, springs cause selected electrodes 12 to advance out of catheter 14.

One or more cables 38 couple electrodes 12 to an electromagnetic energy source 40. A variety of energy sources 40 can be used with the present invention to transfer electromagnetic energy to the interior of a body structure, including but not limited to RF, microwave, ultrasound, coherent light and thermal transfer. Preferably, energy source 40 is a RF generator. When a RF energy source is used, the physician can activate RF energy source 40 by the use of a foot switch (not shown) coupled to RF energy source 40.

One or more sensors 42 may be positioned on an interior or exterior surface of electrode 12, insulation sleeve 32, or be independently inserted into the interior of the body structure. Sensors 42 permit accurate measurement of temperature at a tissue site in order to determine, (i) the extent of ablation, (ii) the amount of ablation, (iii) whether or not further ablation is needed, and (iv) the boundary or periphery of the ablated geometry. Further, sensors 42 prevent non-targeted tissue from being destroyed or ablated.

Sensors 42 are of conventional design, including but not limited to thermistors, thermocouples, resistive wires, and the like. Suitable sensors 42 include a T type thermocouple with copper constantene, J type, E type, K type, fiber optics, resistive wires, thermocouple IR detectors, and the like. It will be appreciated that sensors 42 need not be thermal sensors.

Sensors 42 measure temperature and/or impedance to permit ablation monitoring. This reduces damage to tissue surrounding the targeted ablation mass. By monitoring the temperature at various points within the interior of the body structure the periphery of ablation can be ascertained and it is possible to determine when the ablation is completed. If at any time sensor 42 determines that a desired ablation temperature is exceeded, then an appropriate feedback signal is received at energy source 40 and the amount of energy delivered is regulated.

Ablation apparatus 10 can include visualization capability including but not limited to a viewing scope, an expanded eyepiece, fiber optics, video imaging, and the like.

Additionally, ultrasound imaging can be used to position the electrodes 12 and/or determine the amount of ablation. One or more ultrasound transducers 44 can be positioned in or on electrode 12, catheter 14, or on a separate device. An imaging probe may also be used internally or externally to the selected tissue site. A suitable imaging probe is Model 21362, manufactured and sold by Hewlett Packard Company. Each ultrasound transducer 44 is coupled to an ultrasound source (not shown).

Figure 6:
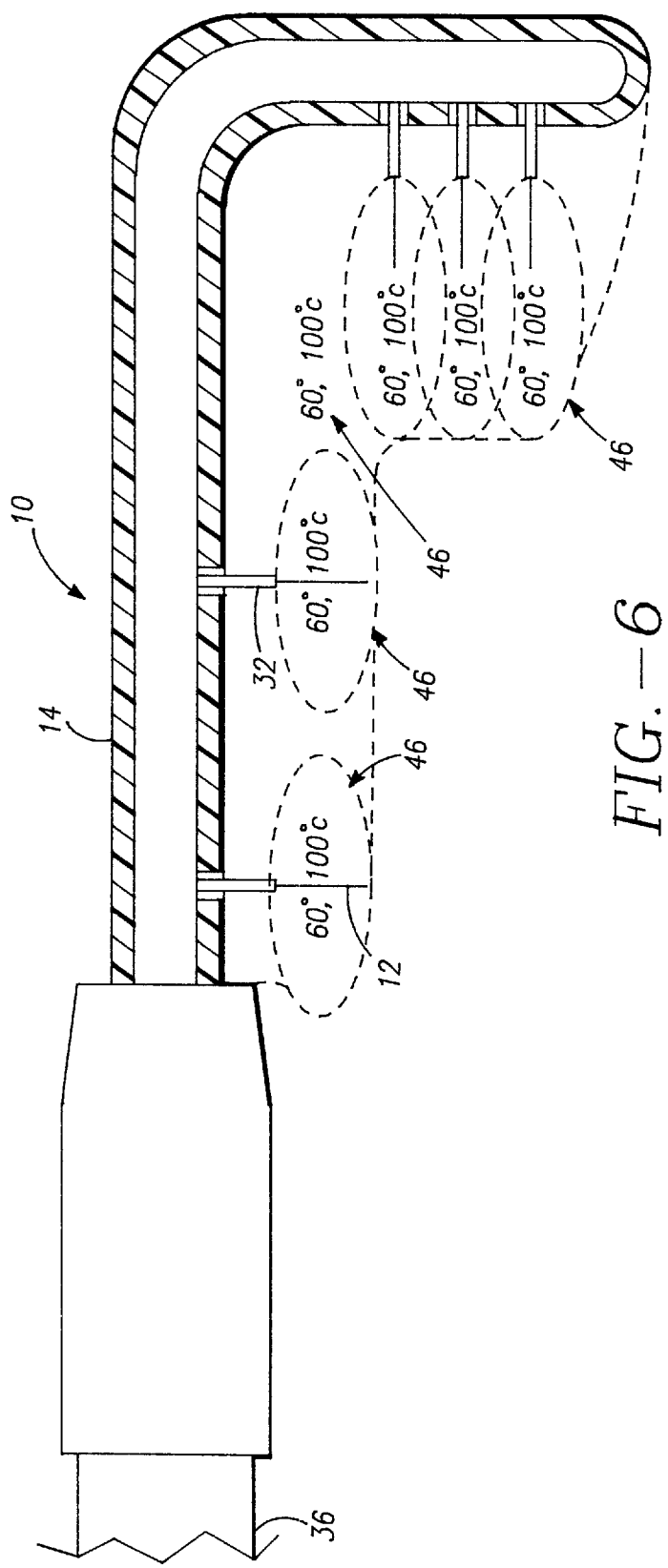
FIG. 6 illustrates the creation of ablation zones with the ablation apparatus shown in FIG. 1(a).
Figure 8:
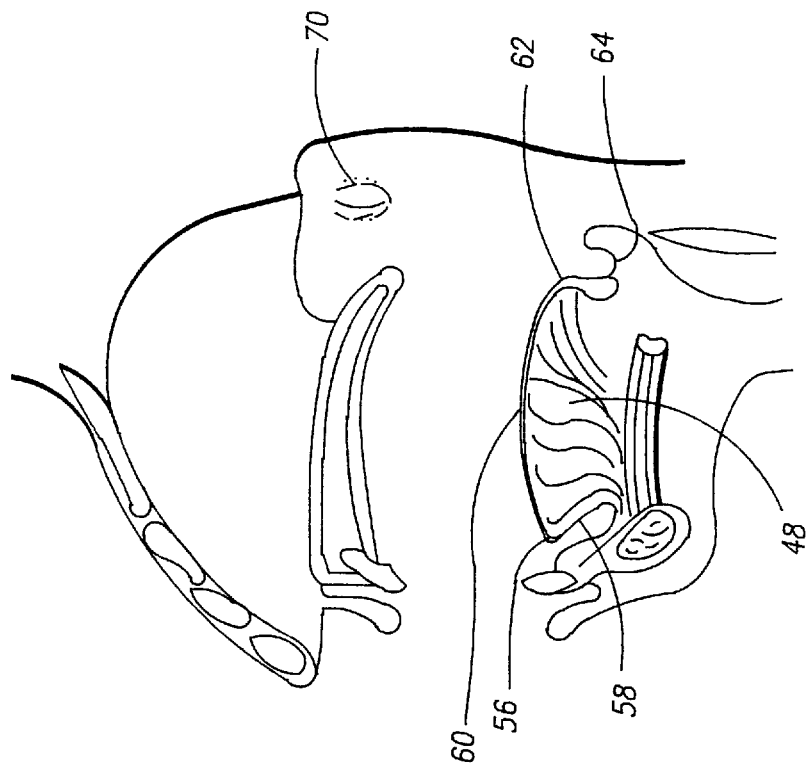
FIG. 8 is a cross-sectional view of the tongue with the mouth open.
Figure 7:
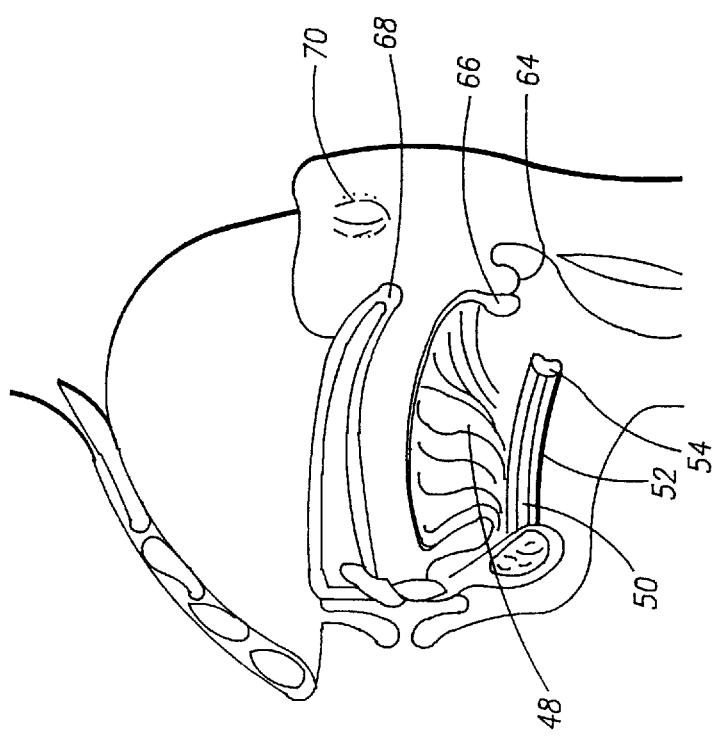
FIG. 7 is a cross-sectional view of the tongue with the mouth closed.
Figure 9:
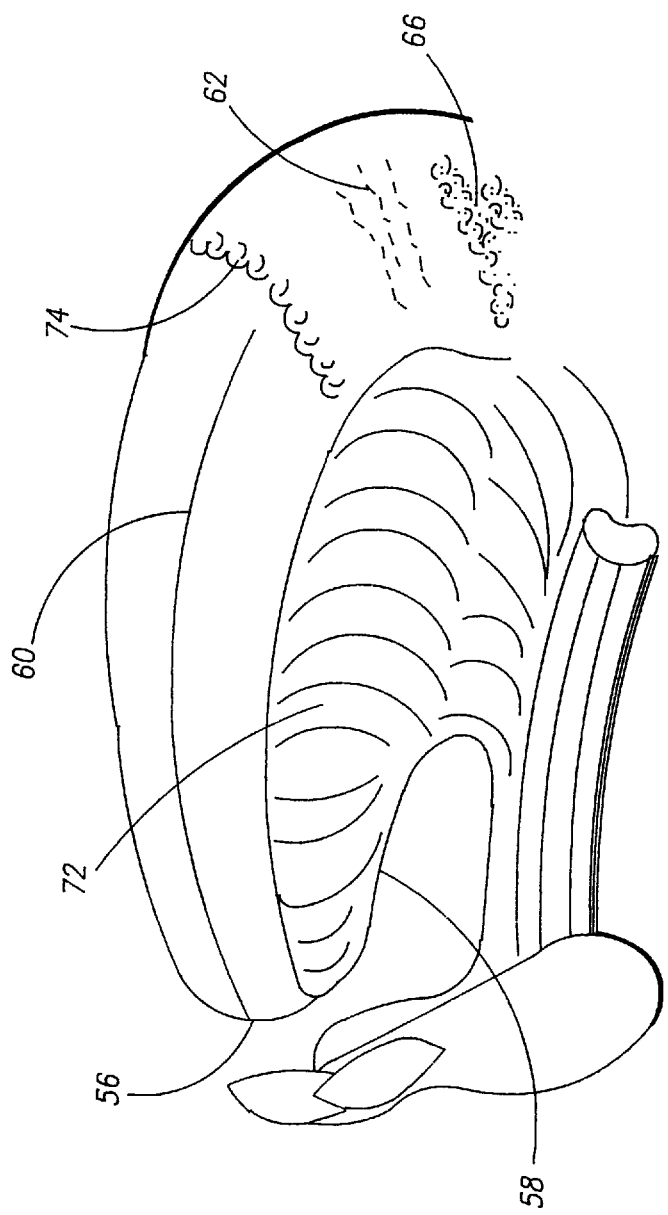
FIG. 9 is a perspective view of the tongue.
Figure 11:
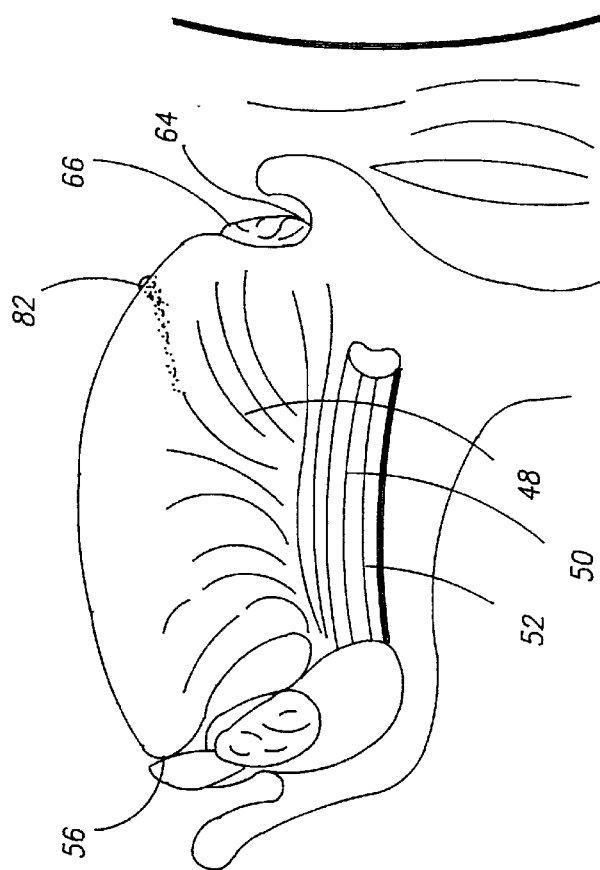
FIG. 11 is a cross-sectional view of the tongue.
Figure 10:
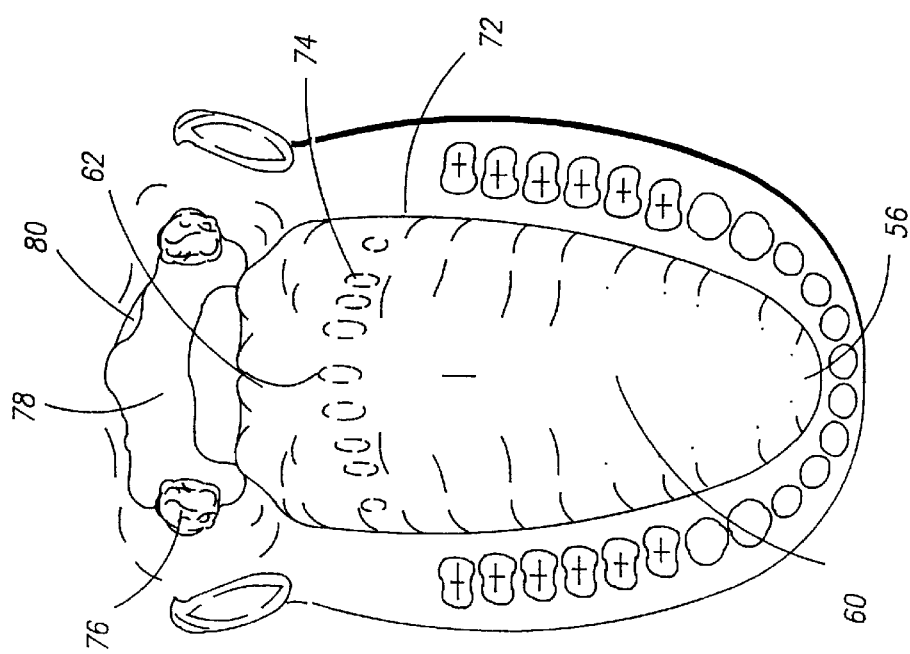
FIG. 10 is a perspective view of the dorsum of the tongue.
Figure 13:
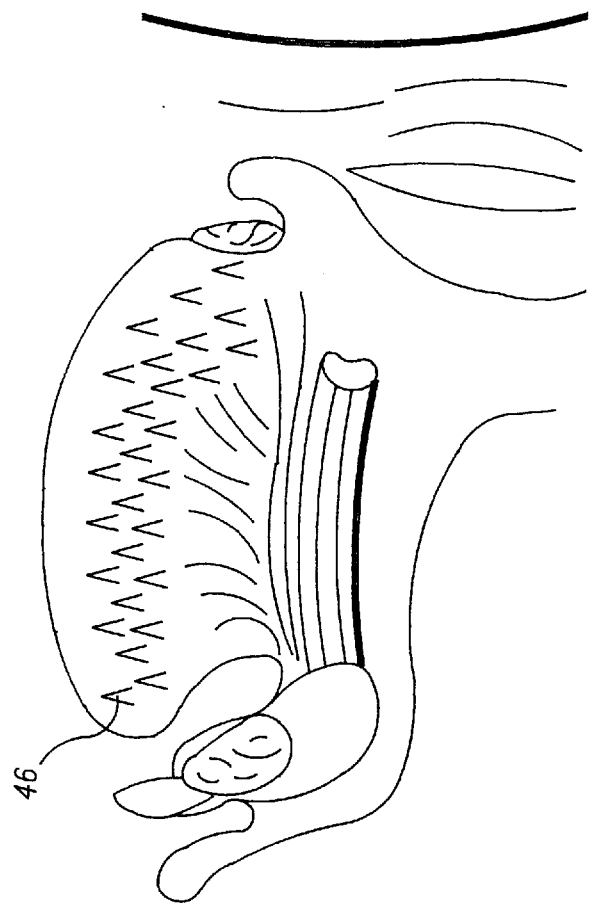
FIG. 13 is a cross-sectional view of the tongue illustrating a plurality of ablation zones.
Figure 12:
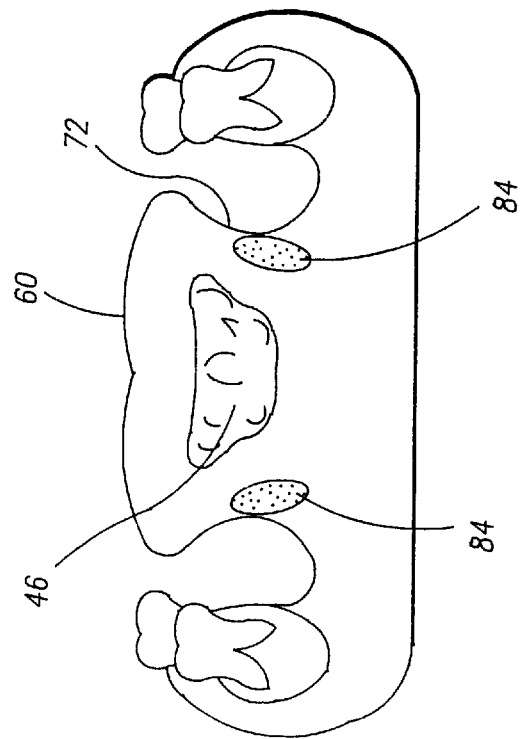
FIG. 12 is a cross-sectional view of the tongue illustrating the location of the hypoglossal nerves and the creation of an ablation zone.
Figure 15:
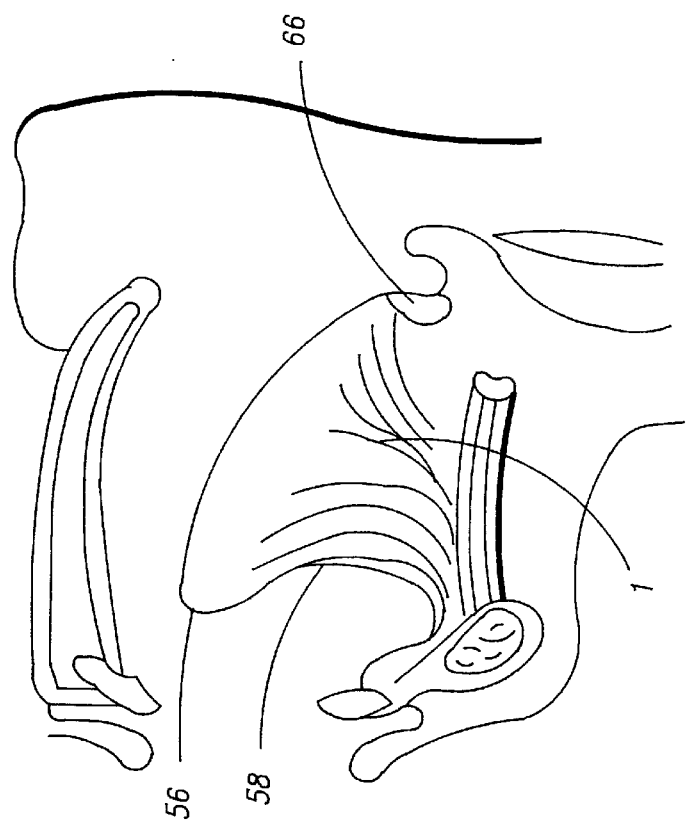
FIG. 15 is a cross-sectional view of the tongue.
Figure 14:
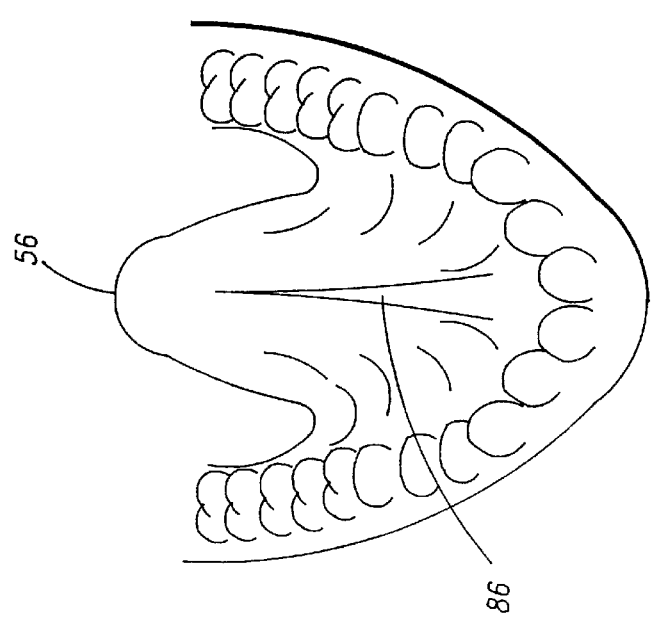
FIG. 14 is a perspective view of the ventral surface of the tongue.

With reference now to FIG. 6 catheter 14 is shown as being introduced into the oral cavity and multiple RF electrodes 12 are advanced into the interior of the tongue creating different ablation zones 46. Ablation apparatus 10 can be operated in either bipolar or monopolar modes. In FIG. 6, electrodes 12 are operated in the bipolar mode, creating sufficient ablation zones 46 to debulk the tongue without affecting the hypoglossal nerves and creating a larger airway passage. With this debulking, the back of the tongue moves in a forward direction away from the air passageway. The result is an increase in the cross-sectional diameter of the air passageway.

Ablation apparatus 10 can also be operated in the monopolar mode. A groundpad can be positioned in a convenient place such as under the chin. A single electrode 12 is positioned in the tongue to create a first ablation zone 46. Electrode 12 can then be retracted from the interior of the tongue, catheter 14 moved, and electrode 12 is then advanced from catheter 14 into another interior section of the tongue. A second ablation zone 46 is created. This procedure can be completed any number of times to form different ablation regions in the interior of the tongue. More than one electrode 12 can be introduced into the tongue and operated in the bipolar mode. Electrodes 12 are then repositioned in the interior of the tongue any number of times to create a plurality of connecting or non-connecting ablation zones 46.

Referring now to FIGS. 7 through 15, various anatomical views of the tongue and other structures are illustrated. The different anatomical structures are as follows: the genioglossus muscle, or body of the tongue is denoted as 48; the geniohyoid muscle is 50; the mylohyoid muscle is 52; the hyoid bone is 54; the tip of the tongue is 56; the ventral surface of the tongue is denoted as 58; the dorsum of the tongue is denoted as 60; the inferior dorsal of the tongue is denoted as 62; the reflex of the vallecula is 64; the lingual follicles are denoted as 66; the uvula is 68; the adenoid area is 70; the lateral border of the tongue is 72; the circumvallate papilla is 74, the palatine tonsil is 76; the pharynx is 78; the redundant pharyngeal tissue is 80; the foramen cecum is 82; the hypoglossal nerve is 84, and the lingual frenum of the tongue is 86.

Dorsum 60 is divided into an anterior ⅔ and inferior dorsal 62. The delineation is determined by circumvallate papilla 74 and foramen cecum 82. Inferior dorsal 62 is the dorsal surface inferior to circumvallate papilla 74 and superior reflex of the vallecula 64. Reflex of the vallecula 64 is the deepest portion of the surface of the tongue contiguous with the epiglottis. Lingual follicles 66 comprise the lingual tonsil.

Catheter 14 can be introduced through the nose or through the oral cavity. Electrodes 12 can be inserted into an interior of the tongue through dorsum surface 60, inferior dorsal surface 62, ventral surface 58, tip 56 or geniohyoid muscle 50. Additionally, electrodes may be introduced into an interior of lingual follicles 66 and into adenoid area 70. Once electrodes 12 are positioned, insulation sleeve 32 may be adjusted to provided a desired electromagnetic energy delivery surface 30 for each electrode 12.

Ablation zones 46 are created without damaging hypoglossal nerves 84. This creates a larger air way passage and provides a treatment for sleep apnea.

In all instances, the positioning of electrodes 12, as well as the creation of ablation zones 46 is such that hypoglossal nerves 84 are not ablated or damaged. The ability to swallow and speak is not impaired.

Figure 16:
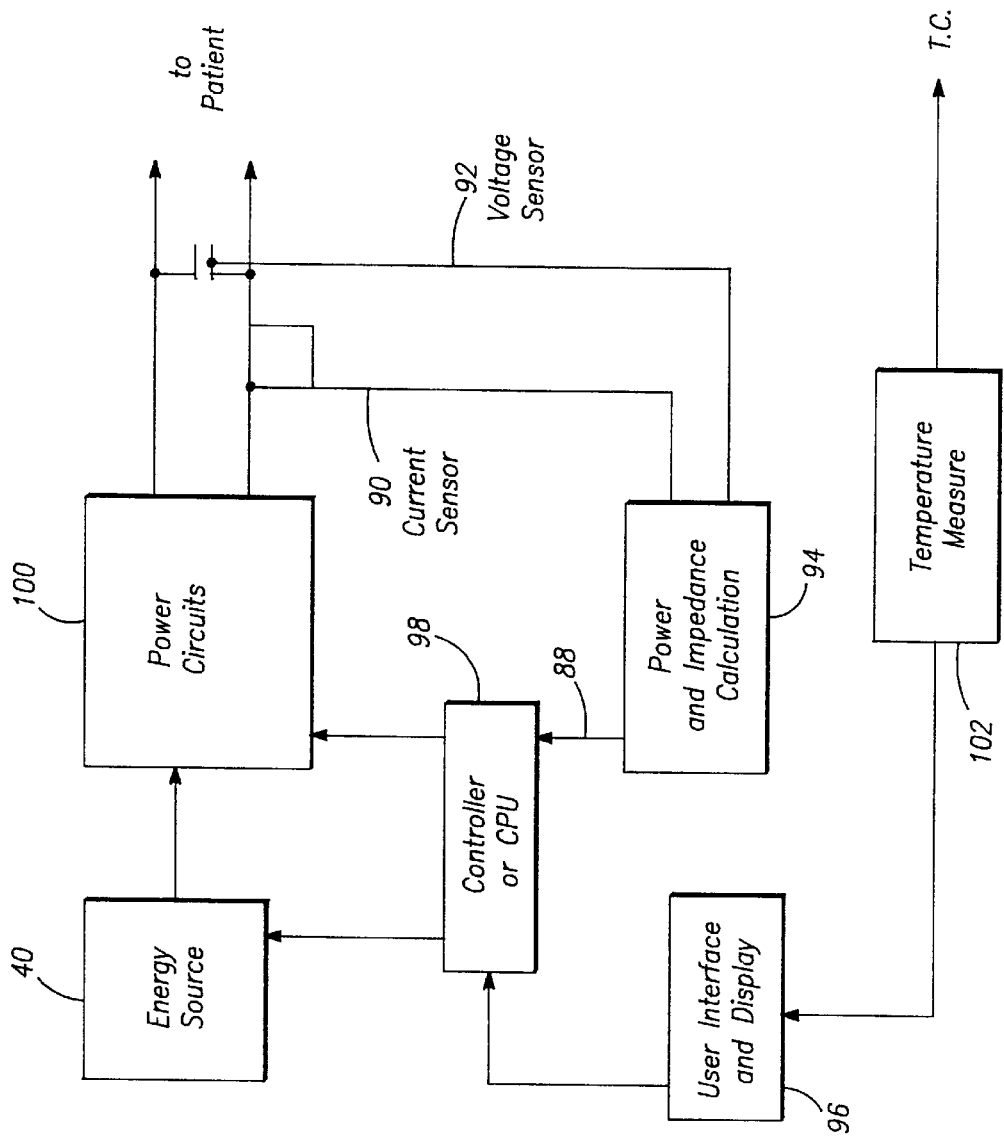
FIG. 16 is a perspective view of the dorsum surface of the tongue, and the relative positioning of electrodes into the dorsum surface of the tongue.

FIG. 16 illustrates placement of electrodes on the dorsum surface 60 of the tongue. The first electrode is positioned 0.5 cm proximal to the circumvallate pappilla. The other electrodes are spaced 1.6 cm apart and are 1 cm off a central axis of the tongue. In one embodiment, 465 MHz RF was applied. The temperature at the distal end of electrode 12 was about 100 degrees C. The temperature at the distal end of the insulation sleeve 32 was about 60 degrees C. In another embodiment, the temperature at the distal end of insulation sleeve 32 was 43 degrees C and above. RF energy can be applied as short duration pulses with low frequency RF. Precise targeting of a desired ablation site is achieved. One or more electrodes 12 may be used to create volumetric three-dimensional ablation. A variety of ablation geometries are possible, including but not limited to rectilinear, polyhedral, redetermined shapes, symmetrical and non-symmetrical.

Figure 17:
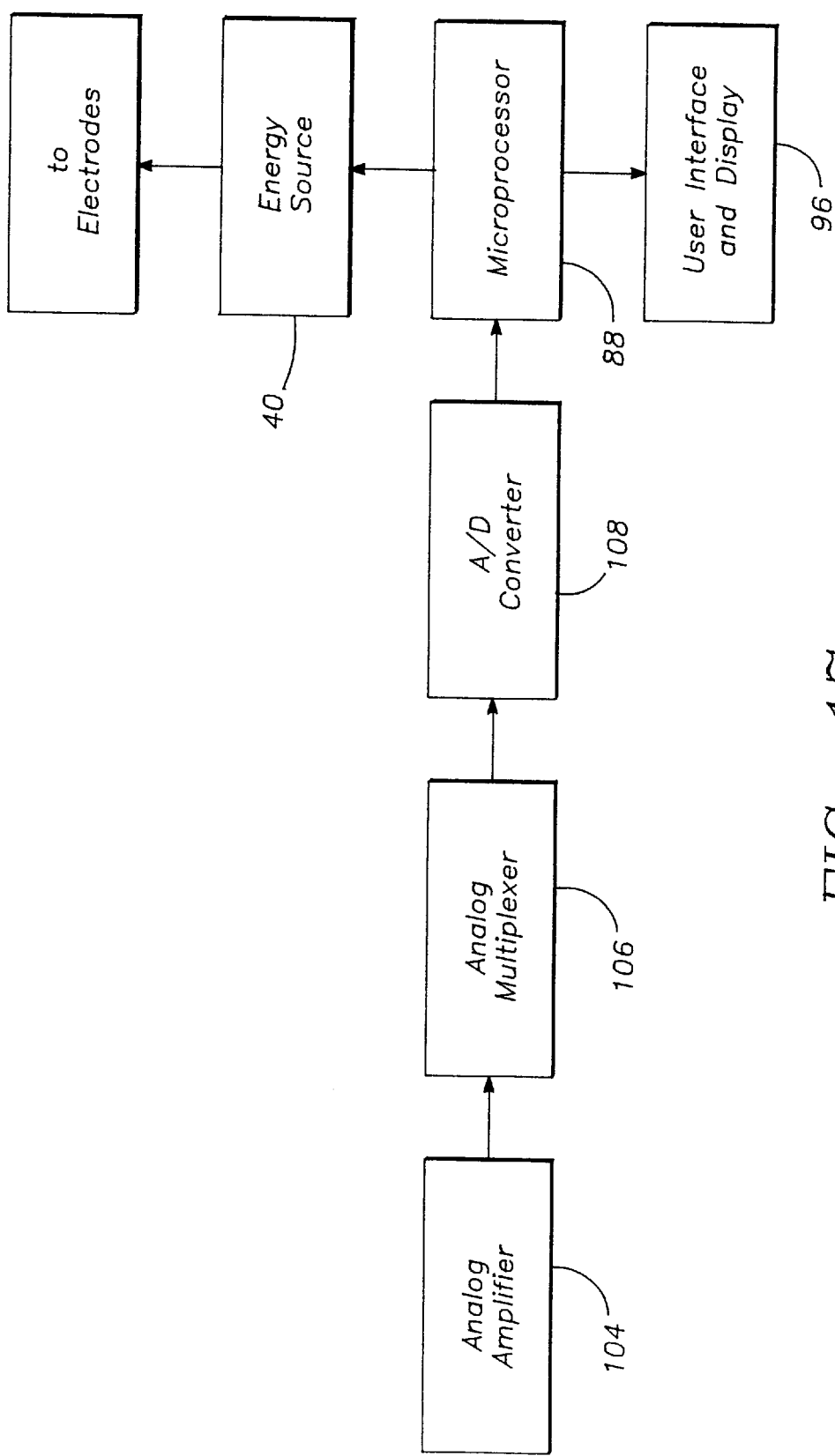
FIG. 17 is a block diagram of a feedback control system useful with the methods of the present invention.
Figure 18:
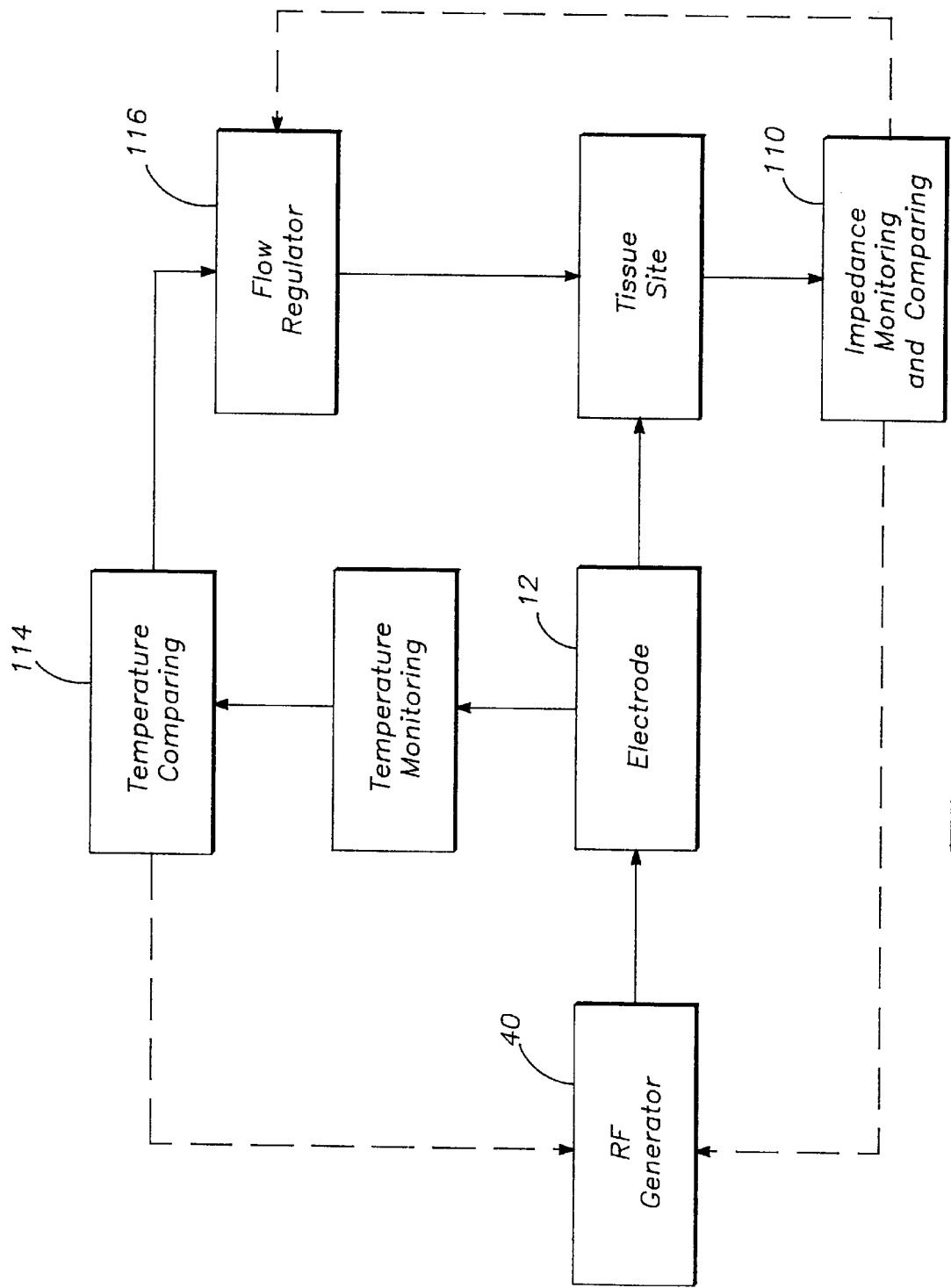
FIG. 18 is a block diagram illustrating an analog amplifier, analog multiplexer and microprocessor used with the feedback control system of FIG. 17.

Referring now to FIGS. 17 and 18 an open or closed loop feedback system couples sensors 42 to energy source 40. The temperature of the tissue, or of electrode 12 is monitored, and the output power of energy source 40 adjusted accordingly. Additionally, the level of disinfection in the oral cavity can be monitored. The physician can, if desired, override the closed or open loop system. A microprocessor can be included and incorporated in the closed or open loop system to switch power on and off, as well as modulate the power. The closed loop system utilizes a microprocessor 88 to serve as a controller, watch the temperature, adjust the RF power, look at the result, refeed the result, and then modulate the power.

With the use of sensors 42 and the feedback control system a tissue adjacent to RF electrodes 12 can be maintained at a desired temperature for a selected period of time without impeding out. Each RF electrode 12 is connected to resources which generate an independent output for each RF electrode 12. An output maintains a selected energy at RF electrodes 12 for a selected length of time.

Current delivered through RF electrodes 12 is measured by current sensor 90. Voltage is measured by voltage sensor 92. Impedance and power are then calculated at power and impedance calculation device 94. These values can then be displayed at user interface and display 96. Signals representative of power and impedance values are received by a controller 98.

A control signal is generated by controller 98 that is proportional to the difference between an actual measured value, and a desired value. The control signal is used by power circuits 100 to adjust the power output in an appropriate amount in order to maintain the desired power delivered at respective RF electrodes 12.

In a similar manner, temperatures detected at sensors 42 provide feedback for maintaining a selected power. The actual temperatures are measured at temperature measurement device 102, and the temperatures are displayed at user interface and display 96. A control signal is generated by controller 98 that is proportional to the difference between an actual measured temperature, and a desired temperature.

The control signal is used by power circuits 100 to adjust the power output in an appropriate amount in order to maintain the desired temperature delivered at the respective sensor. A multiplexer can be included to measure current, voltage and temperature, at the numerous sensors 42, and energy can be delivered to RF electrodes 12 in monopolar or bipolar fashion.

Controller 98 can be a digital or analog controller, or a computer with software. When controller 98 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 96 includes operator controls and a display. Controller 98 can be coupled to imaging systems, including but not limited to ultrasound, CT scanners, X-ray, MRI, mammographic X-ray and the like. Further, direct visualization and tactile imaging can be utilized.

The output of current sensor 90 and voltage sensor 92 is used by controller 98 to maintain a selected power level at RF electrodes 12. The amount of RF energy delivered controls the amount of power. A profile of power delivered can be incorporated in controller 98, and a preset amount of energy to be delivered can also be profiled.

Circuitry, software and feedback to controller 98 result in process control, and the maintenance of the selected power that is independent of changes in voltage or current, and are used to change, (i) the selected power, (ii) the duty cycle (on-off and wattage), (iii) bipolar or monopolar energy delivery, and (iv) infusion medium delivery, including flow rate and pressure. These process variables are controlled and varied, while maintaining the desired delivery of power independent of changes in voltage or current, based on temperatures monitored at sensors 42.

Current sensor 90 and voltage sensor 92 are connected to the input of an analog amplifier 104. Analog amplifier 104 can be a conventional differential amplifier circuit for use with sensors 42. The output of analog amplifier 104 is sequentially connected by an analog multiplexer 106 to the input of A/D converter 108. The output of analog amplifier 104 is a voltage which represents the respective sensed temperatures. Digitized amplifier output voltages are supplied by A/D converter 108 to microprocessor 88. Microprocessor 88 may be a type 68HCII available from Motorola. However, it will be appreciated that any suitable microprocessor or general purpose digital or analog computer can be used to calculate impedance or temperature.

Microprocessor 88 sequentially receives and stores digital representations of impedance and temperature. Each digital value received by microprocessor 88 corresponds to different temperatures and impedances.

Calculated power and impedance values can be indicated on user interface and display 96. Alternatively, or in addition to the numerical indication of power or impedance, calculated impedance and power values can be compared by microprocessor 88 with power and impedance limits. When the values exceed predetermined power or impedance values, a warning can be given on user interface and display 96, and additionally, the delivery of RF energy can be reduced, modified or interrupted. A control signal from microprocessor 88 can modify the power level supplied by energy source 40.

Figure 19:
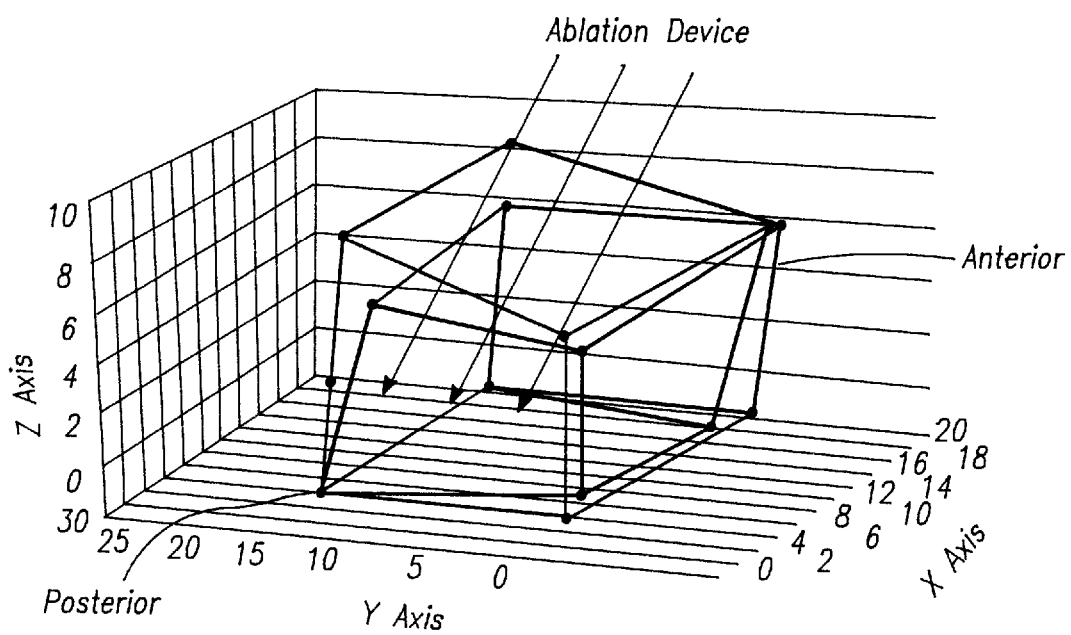
FIG. 19 is a block diagram of a temperature/impedance feedback system that can be used to control cooling medium flow rate through the catheter of FIG. 1.

FIG. 19 illustrates a block diagram of a temperature/impedance feedback system that can be used to control cooling medium flow rate through catheter 14. Electromagnetic energy is delivered to electrode 12 by energy source 44, and applied to tissue. A monitor 110 ascertains tissue impedance, based on the energy delivered to tissue, and compares the measured impedance value to a set value. If the measured impedance exceeds the set value a disabling signal 112 is transmitted to energy source 40, ceasing further delivery of energy to electrode 12. If measured impedance is within acceptable limits, energy continues to be applied to the tissue. During the application of energy to tissue sensor 42 measures the temperature of tissue and/or electrode 12. A comparator 114 receives a signal representative of the measured temperature and compares this value to a pre-set signal representative of the desired temperature. Comparator 114 sends a signal to a flow regulator 116 representing a need for a higher cooling medium flow rate, if the tissue temperature is too high, or to maintain the flow rate if the temperature has not exceeded the desired temperature.

EXAMPLE 1

Ablation apparatus 10 was used to determine two-dimensional shrinkage of a bovine. RF volumetric reduction was achieved using a single needle electrode. Four minature ultrasonic crystals were positioned to form a square. Measurements were taken at control and post volumetric reduction at 15 watts initially with a 13% volumetric reduction, and 15 watts for 4 hours with an additional 4% volumetric reduction. A total 17% volumetric reduction was achieved.

EXAMPLE 2

Ablation apparatus 10 was used to determine three-dimensional shrinkage of a bovine tongue. RF volumetric reduction was achieved with a single needle electrode with eight minature ultrasonic crystals, creating a cube. Application of 16 watts initially produced a 17% volumetric reduction of the tongue, 25 watts applied initially produced a 25% volumetric reduction, and 25 watts after hours produced an additional 4% reduction, for a total volumetric reduction of 29%.

EXAMPLE 3

A 35% volumetric reduction was achieved in porcine in vivo, with three dimensional gross at 20 watts initial application.

Figure 20:
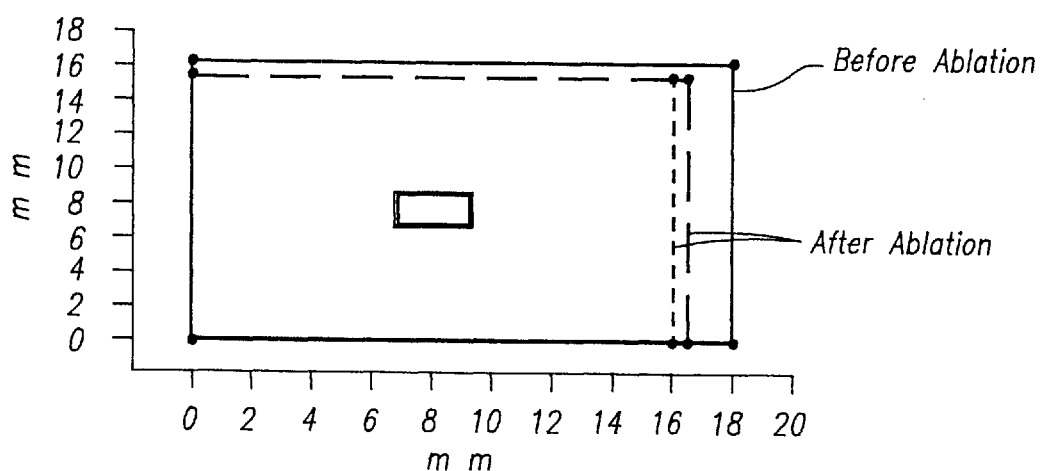
FIG. 20 is a three dimensional graph illustrating the percent shrinkage of the tongue following RF ablation.

Referring now to FIG. 20, ablation volume dimensions were measured with a multidimensional digital sonomicrometry. An average decrease in the Z direction was 20%, and volume shrinkage was 26%. Three-dimensional shrinkage of tongue tissue due to in vivo RF ablation with the needle, ablation with 20 Watts) is presented in FIG. 20. Control volume before ablation is compared with a post-ablation volume.

Figure 21:
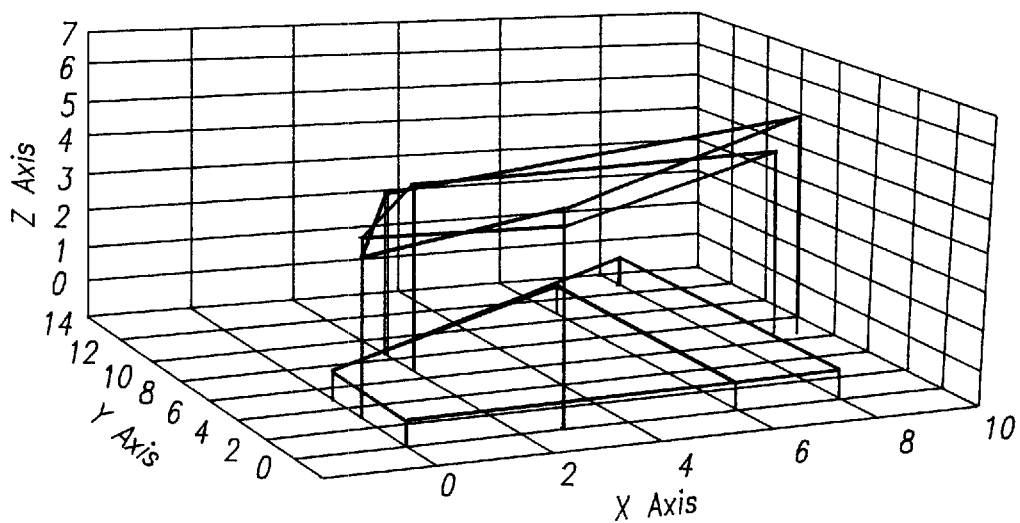
FIG. 21 is a graph illustrating two-dimensional shrinkage of bovine tongue tissue with RF ablation.

FIG. 21 illustrates two-dimensional shrinkage of a bovine tongue tissue due to RF ablation with a needle electrode. The before and after ablation results are illustrated.

Figure 22:
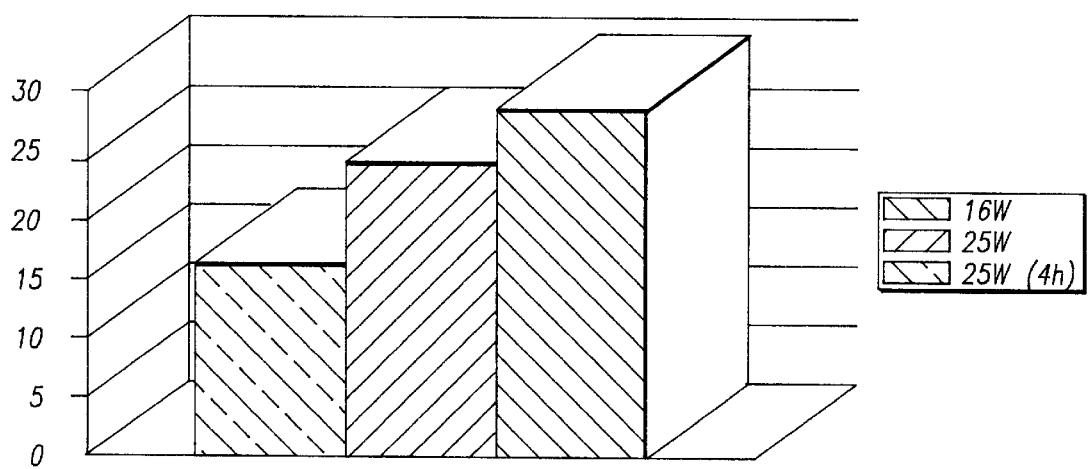
FIG. 22 is a graph illustrating three-dimensional shrinkage of bovine tongue tissue due to RF ablation.

FIG. 22 illustrates in graph form ablation at 16 Watts resulted in a 17% volume shrinkage of the tissue in post-ablation verses control. Ablation at 25 watts resulted in a 25% volume shrinkage after ablation. An additional 4% area shrinkage was obtained after in long-term post ablation (4 hours) verses post-ablation.

Figure 23:
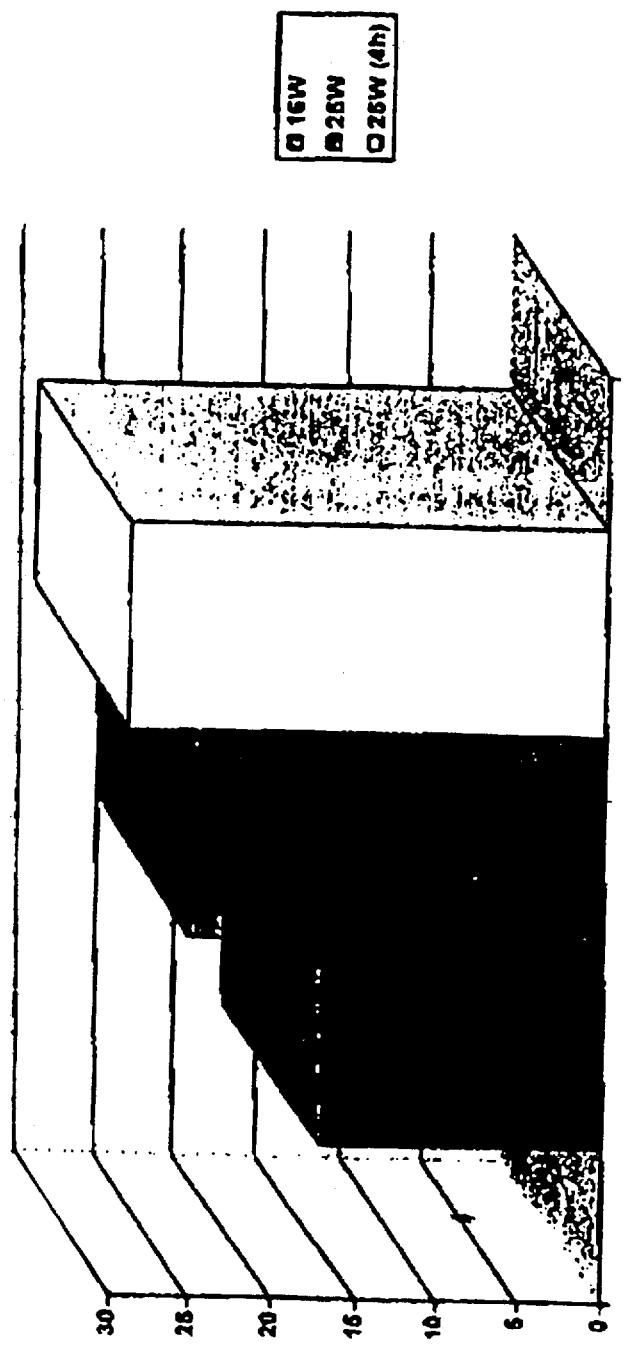
FIG. 23 is a graph illustrating percent volume change in a tongue following RF ablation.

FIG. 23 illustrates a percent volume change after RF ablation. 16 Watts, ablation at 16 Watts for 20 minutes; 25 Watts, ablation at 25 Watts for 20 minutes; 25 Watts (4 hours), and long tern post ablation (4 hours after 25 Watts ablation).

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for ablating at least a portion of an interior of a body structure, comprising:

a catheter including a catheter tissue interface surface and a port formed in the catheter tissue interface surface;

an energy delivery device at least partially positioned in the interior of the catheter and configured to be advanced and retracted in and out of the port, the energy delivery device including an energy delivery surface;

a disinfectant medium introduction member coupled to the catheter and to a source of a disinfectant medium and including a distal end configured to extend into an oral cavity;

an energy delivery device advancement and retraction device at least partially positioned in the interior of the catheter; and a cable coupled to the electrode.

2. The apparatus of claim 1, wherein the disinfectant medium introduction member is coupled to the catheter.

3. The apparatus of claim 1, wherein the disinfectant medium introduction member is a lumen at least partially positioned in an interior of the catheter.

4. The apparatus of claim 1, wherein the disinfectant medium introduction member is at least partially positioned at an exterior surface of the catheter.

5. The apparatus of claim 1, wherein the disinfectant medium introduction member includes a disinfectant medium introduction port.

6. The apparatus of claim 5, wherein the disinfectant medium introduction port is configured to introduce the disinfectant medium into a selected portion of the oral cavity.

7. The apparatus of claim 1, wherein the disinfectant medium introduction member is an introducer with a lumen configured to deliver the disinfectant medium throughout the oral cavity.

8. The apparatus of claim 1, wherein the disinfectant medium introduction member is configured to deliver a selected wavelength of electromagnetic energy to the oral cavity.

9. The apparatus of claim 1, wherein the disinfectant medium introduction member is an optical fiber coupled to a UV energy source.

10. The apparatus of claim 1, wherein the disinfectant medium introduction member is a fluid conduit configured to deliver a disinfectant solution into a selected region of the oral cavity.

11. The apparatus of claim 1, further comprising:

a cooling element including a cooling medium inlet conduit and a cooling medium exit conduit both extending through an interior of the catheter forming at least a partial cooled catheter tissue interface surface, wherein the energy delivery surface is thermally isolated from the cooling element.

12. The apparatus of claim 1, further comprising:

an insulation sleeve positioned in a surrounding relationship to at least a portion of an exterior surface of the energy delivery device.

13. The apparatus of claim 1, further comprising:
a sensor positioned at a distal end of the energy delivery device.

14. The apparatus of claim 12, further comprising:
a first sensor positioned at a distal end of the energy delivery device and a second sensor positioned at a distal end of the insulation sleeve.

15. The apparatus of claim 1, wherein the energy delivery device is an configured to be coupled to a RF energy source.

16. The apparatus of claim 1, wherein the energy delivery device is an antenna configured to be coupled to a microwave energy source.

17. The apparatus of claim 1, wherein two or more energy delivery devices are each advanced into a different interior region of a tongue.

18. The apparatus of claim 1, wherein the energy delivery device is a waveguide configured to be coupled to a light source.

19. The apparatus of claim 1, wherein the energy delivery device is an ultrasound emitter configured to be coupled to a ultrasound source.

20. A method for reducing a volume of a body structure, comprising:
providing an ablation apparatus including a catheter with a catheter tissue interface surface, and an energy delivery device with an energy delivery surface at least partially positioned in an interior of the catheter and advanceable and retractable to and from the catheter into an interior of the body member;
providing a disinfectant medium introduction member coupled to the catheter and configured to introduce a disinfectant medium into at least a portion of an oral cavity;
introducing the disinfectant medium introduction member into the oral cavity;
introducing the ablation apparatus into the oral cavity;
disinfectant at least a portion of the oral cavity sufficiently to reduce an infection of the body member;
advancing the energy delivery surface from the interior of the catheter through a body structure external surface into the interior of the body structure;
delivering sufficient energy from the energy delivery surface into the interior of the body structure to ablate a portion of the interior of the body structure; and
retracting the energy delivery surface from the interior of the body structure.

21. The method of claim 20, wherein the body structure is a tongue.

22. The method of claim 20, wherein the body structure is a soft palate tissue.

23. The method of claim 20, further comprising:
introducing the disinfectant medium into the oral cavity while the energy is supplied to the body member from the energy delivery surface.

24. The method of claim 20, further comprising:
introducing the disinfectant medium into the oral cavity following the delivery of energy to the body member from the energy delivery surface.

25. The method of claim 20, wherein the disinfectant medium is UV energy.

26. The method of claim 20, wherein the disinfectant medium is a disinfectant solution of a disinfectant agent.

27. The method of claim 20, wherein the external body surface is a dorsum surface of the tongue.

28. The method of claim 20, wherein the exterior body surface is a ventral surface of the tongue.

29. The method of claim 20, wherein the exterior surface is an inferior dorsal surface of the tongue.

30. The method of claim 20, wherein sufficient energy is delivered to an interior of the tongue to ablate at least a portion of the interior of tongue with a minimal ablation of a surface of the tongue.

31. The method of claim 30, wherein a taste buds on the surface of the tongue are not ablated.

32. The method of claim 20, wherein the ablation apparatus includes two or more energy delivery devices, each advanced and retracted from a separate port formed in the catheter tissue interface surface.

33. The method of claim 30, wherein the interior of the tongue is sufficiently ablated to increase a cross-sectional area of an airway passage.

34. The method of claim 20, wherein the energy delivery device is an RF electrode configured to be coupled to an RF source.

35. The method of claim 20, wherein the energy delivery device is a microwave antenna configured to be coupled to a microwave source.

36. The method of claim 20, wherein the disinfectant medium introduction member is coupled to the catheter.

37. The method of claim 20, wherein the body structure is a soft palate tissue.

38. The method of claim 20, wherein the body structure is a uvula.

39. The method of claim 20, wherein the energy delivery device is a waveguide configured to be coupled to a light source.

40. The method of claim 20, wherein the energy delivery device is an ultrasound emitter configured to be coupled to an ultrasound source.

* * * * *

UNITED STATES PATENT AND TRADEMARK OFFICE
CERTIFICATE OF CORRECTION

PATENT NO. : 5,836,906
DATED : November 17, 1998
INVENTOR(S) : Stuart D. Edwards It is certified that error appears in the above-identified patent and that said Letters Patent is hereby corrected as shown below:

Title page, item 63, Related U.S. Application Data, Change "Pat. No. 5,683,360" to --Pat. No. 5,707,349--.

Signed and Sealed this

Fourteenth Day of September, 1999

Attest:

Q. TODD DICKINSON

*Attesting Officer*   *Acting Commissioner of Patents and Trademarks*